(12) United States Patent
Molz et al.

(10) Patent No.: US 8,317,830 B2
(45) Date of Patent: Nov. 27, 2012

(54) ORTHOPAEDIC SCREW SYSTEM WITH LINEAR MOTION

(75) Inventors: Fred Molz, Birmingham, AL (US); Randal Betz, Ocean City, NJ (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1359 days.

(21) Appl. No.: 11/468,054

(22) Filed: Aug. 29, 2006

(65) Prior Publication Data
US 2008/0086125 A1 Apr. 10, 2008

(51) Int. Cl.
*A61F 2/30* (2006.01)
(52) U.S. Cl. ........................................ 606/246
(58) Field of Classification Search .......... 606/246–299, 606/60, 70, 71, 300–331; 623/17.11–17.16
See application file for complete search history.

(56) References Cited

U.S. PATENT DOCUMENTS

| 3,829,065 | A | | 8/1974 | Less |
| 4,957,495 | A | | 9/1990 | Kluger |
| 5,090,647 | A | | 2/1992 | Clarke |
| 5,413,576 | A | * | 5/1995 | Rivard ........................ 606/250 |
| 5,490,851 | A | | 2/1996 | Nenov et al. |
| 5,628,740 | A | * | 5/1997 | Mullane ....................... 606/307 |
| 5,630,817 | A | | 5/1997 | Rokegem et al. |
| 5,672,175 | A | * | 9/1997 | Martin ......................... 606/86 A |
| 5,733,286 | A | | 3/1998 | Errico et al. |
| 6,214,004 | B1 | | 4/2001 | Coker |
| 6,224,597 | B1 | * | 5/2001 | Coker ........................... 606/279 |
| 6,554,831 | B1 | * | 4/2003 | Rivard et al. .................. 606/253 |
| 6,585,738 | B1 | | 7/2003 | Mangione et al. |
| 6,729,606 | B1 | | 5/2004 | Durin |
| 2004/0172025 | A1 | | 9/2004 | Drewry et al. |
| 2004/0232276 | A1 | | 11/2004 | Ferris |
| 2005/0101956 | A1 | * | 5/2005 | Simonson ....................... 606/61 |
| 2005/0113835 | A1 | | 5/2005 | Ashman |
| 2005/0277927 | A1 | | 12/2005 | Guenther et al. |
| 2005/0283157 | A1 | | 12/2005 | Coates et al. |
| 2006/0149229 | A1 | * | 7/2006 | Kwak et al. .................... 606/61 |
| 2006/0282073 | A1 | * | 12/2006 | Simanovsky ................... 606/61 |

FOREIGN PATENT DOCUMENTS

| EP | 0 572 790 A | 12/1993 |
| WO | 2006/073593 A | 7/2006 |

OTHER PUBLICATIONS

European Patent Office, International Searching Authority, Notification of Transmittal of the International Search Report and the Written Opinion of the International Searching Authority, or the Declaration, International Application No. PCT/US2007/076931, International Search report mailing date Mar. 19, 2008.

* cited by examiner

*Primary Examiner* — Kevin T Truong
*Assistant Examiner* — Christopher Beccia (57) ABSTRACT

Devices, methods and systems for stabilizing at least a portion of the spinal column are provided. Devices include seats and coupling members for engaging an elongate member. Systems include an elongate member sized to span a distance between at least two vertebral bodies and being at least partially formed of a flexible material. One or more seats can include rollers to allow relative movement of the rod and the seat.

35 Claims, 6 Drawing Sheets

ORTHOPAEDIC SCREW SYSTEM WITH LINEAR MOTION

BACKGROUND

The present invention relates generally to the field of systems and methods for the treatment of the spine and other general orthopedic applications, and in some embodiments, to methods and systems for interconnecting and securing two or more vertebra of the spine.

The spine is subject to various pathologies that compromise its load bearing and support capabilities. Such pathologies of the spine include, for example, degenerative diseases, tumors and, of course, fractures and dislocations attributable to physical trauma. In the treatment of spinal pathologies, malformations, or injuries affecting spinal motion segments, it has long been known to remove some or all of a degenerated, ruptured or otherwise failing disc. It is also known that artificial discs, fusion implants, or other interbody devices can be placed into the disc space after disc material removal. External stabilization of spinal segments alone or in combination with interbody devices also provide advantages. Elongated rigid plates, rods and other devices have been helpful in the stabilization and fixation of a spinal motion segment.

While the stabilization systems of the prior art are a step in the right direction, there remains room for improvement. For example, if a patient is still growing, their spine may elongate, resulting in undesired effects on nearby stabilization systems. Other types of spinal movement, such as flexion and extension, can also affect the stabilized spine. Further still, the geometric and dimensional features of stabilization systems and patient anatomy often constrain the surgeon during surgery and prevent optimal placement, attachment and loading of the spinal motion segment.

Thus, there is a general need in the industry to provide systems and methods for stabilizing a spinal motion segment that address one or more of the needs discussed above. There is also a need for improved devices for connecting longitudinal members to the spinal column. There is also a need for stabilization devices that allow segmental motion to be maintained after attachment thereto. There are further needs for stabilization devices that maintain desired corrective forces on the spinal motion segment. The present invention is directed to meeting these needs and/or other needs in a novel and unobvious manner.

SUMMARY

In one embodiment, a system is provided for stabilizing a spinal motion segment. The system includes a rod sized to span a distance between a plurality of vertebrae of the spinal motion segment, and a plurality of attachment mechanisms for securing the rod to the plurality of vertebrae. Each of the plurality of attachment mechanisms includes a seat for securing to the rod and a vertebrae engaging member for securing to the vertebrae. At least one of the attachment mechanisms includes a first roller for allowing the rod to move in a linear direction.

In another embodiment, a system for stabilizing a spinal motion segment is provided. The system includes a rod sized to span a distance between a first and second vertebrae of the spinal motion segment, a first anchor for securing the rod to the first vertebrae, and a second anchor for securing the rod to the second vertebrae. The first anchor includes a first vertebrae engaging member for securing to the first vertebrae and a first seat for communicating with the rod. The first seat includes a first roller for allowing the rod to move in a transverse direction relative to the first vertebrae engaging member.

In some embodiments, the system further includes a third anchor for securing the rod to the third vertebrae. The second anchor includes a second vertebrae engaging member for securing to the second vertebrae and a second seat for communicating with the rod. The second seat includes a second roller for allowing the rod to move in a transverse direction relative to the second vertebrae engaging member.

In one embodiment, a method is provided for stabilizing a spinal motion segment. The method includes spanning a distance between a first and second vertebrae of the spinal motion segment with a rod, securing the rod to the first vertebrae with a first anchor, and securing the rod to the second vertebrae with a second anchor. The first anchor includes a first vertebrae engaging member for securing to the first vertebrae and a first seat for communicating with the rod, the first seat including a first roller for allowing the rod to move in a transverse direction relative to the first vertebrae engaging member.

Additional embodiments are included in the attached drawings and the description provided below.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. It is also emphasized that the drawings appended illustrate only typical embodiments of this invention and are therefore not to be considered limiting in scope, for the invention may apply equally well to other embodiments.

DETAILED DESCRIPTION

For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. Furthermore, the depiction of one or more elements in close proximity to each other does not otherwise preclude the existence of intervening elements. Also, reference numbers may be repeated throughout the embodiments, which does not by itself indicate a requirement that features of one embodiment apply to another embodiment, even if they share the same reference number.

Figure 1:
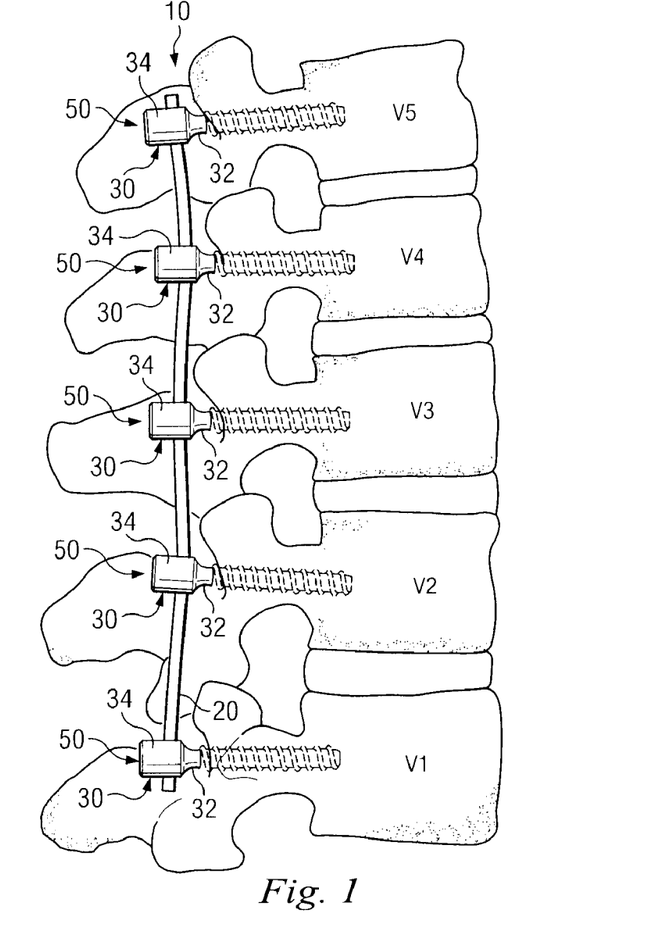
FIG. 1 is a lateral view of a spinal motion segment with a spinal fixation system according to one or more embodiments of the present invention.

Referring to FIG. 1, the reference numeral 10 refers to a spinal stabilization system according to one embodiment of the present invention. The spinal stabilization system 10 is capable of stabilizing a portion of a vertebral column while providing additional features and capabilities such as supporting continued growth of the column. Stabilization system 10 is shown attached to a spinal motion segment that extends across a plurality of vertebrae V1, V2, V3, V4, V5. Stabilization system 10 includes an elongate member (hereinafter referred to as a "rod") 20 secured to a plurality of attachment mechanisms. The rod 20 is secured to the attachment mechanisms (hereinafter referred to as "anchors") 30 with a coupling member 50. One or more of the anchors 30 and/or coupling members 50 may allow a limited amount of linear movement there between, as discussed in greater detail below. Each anchor is further engaged to a respective one of the vertebrae V1, V2, V3, V4, V5.

It should be understood that system 10 may be utilized in all regions of the spine, including the cervical, thoracic, lumbar, and lumbo-sacral regions. It should also be understood that system 10 may extend across a spinal motion segment having only two vertebrae or more than two vertebrae. In some embodiments, two or more stabilization systems may be employed simultaneously along the same spinal motion segment. Additionally, although system 10 is shown in FIG. 1 as having application in a posterior region of the spinal motion segment, system 10 may alternatively be applied in other surgical approaches and combinations of surgical approaches to the spinal motion segment such that one or more stabilization systems 10 are attached to the anterior, antero-lateral, lateral, and/or postero-lateral portions of the spinal motion segment.

Stabilization system 10 allows at least small degrees of linear spinal motion in the spinal motion segment to which it is attached since system 10 includes the rod 20 that is at least partially slidable or movable between one or more anchors 30. It should be understood that stabilization system 10 can be used in conjunction with fusion or non-fusion treatment of the spine. The rod 20, anchors 30 and coupling members 50 can also be formed from any suitable biocompatible material. Such material includes metals such as stainless steel or titanium; polymers such as polyester and polyethylene; superelastic metals or alloys such as nitinol; and resorbable synthetic materials such as suture material and polylactic acid.

Figure 2:
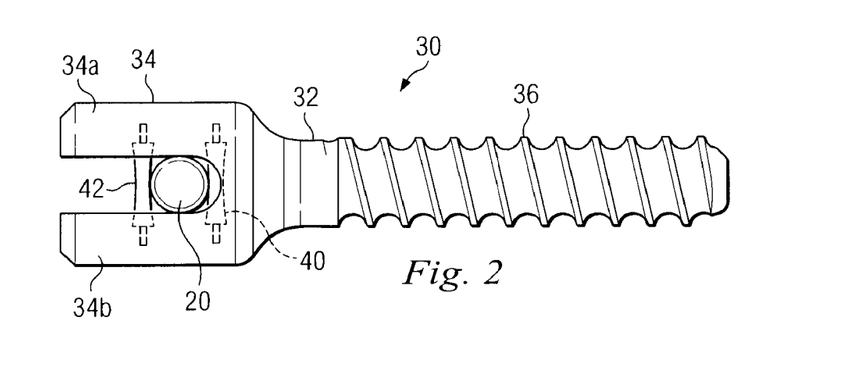
FIG. 2 is side view of an attachment mechanism according to one embodiment of the present invention.
Figure 3:
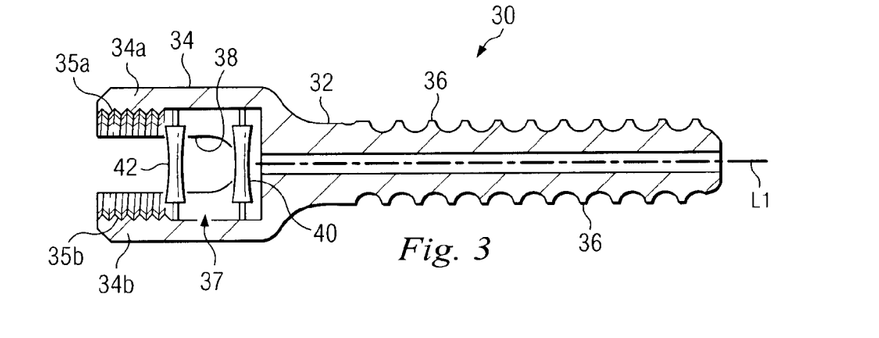
FIG. 3 is a cross-sectional view of the attachment mechanism of FIG. 2.

Referring to FIGS. 2-3, shown therein are various details of the anchor 30 according to a first embodiment of the present invention. The anchor 30 includes an elongated shaft 32 and a rod receiving portion in the form of a seat 34. Shaft 32 can include an external thread form 36 in the form of a single thread turn or a plurality of discrete threads. Different or additional engaging structures along shaft 32 are also contemplated, such as barbs or pivoting gulls, so long as shaft 32 can engage the bony tissue of the vertebra to which anchor 30 is attached. In an alternate form, shaft 32 is in the form of a spinal hook.

In the illustrated embodiment, seat 34 includes a first arm 34a and a second arm 34b. The arms 34a, 34b define internally threaded sections 35a, 35b, respectively, and a roller section 37 positioned in a U-shaped passage 38 extending between the arms. The roller section 37 provides an area in which one or more rollers can be provided. A roller refers to any mechanism that allows relative movement between the anchor 30 and the rod 20. In the present embodiment, the roller section 37 includes a first bar-type roller 40 and a second bar-type roller 42. As shown in FIG. 2, the bar-type rollers 40, 42 are rotatable so that the rod 20 can move in a linear motion there between.

Figure 4:
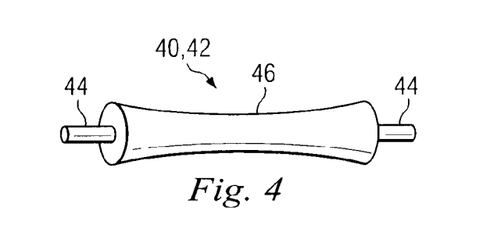
FIGS. 4 and 5 are side views of different embodiments of bar-type rollers for use with the attachment mechanism of FIG. 2.
Figure 5:
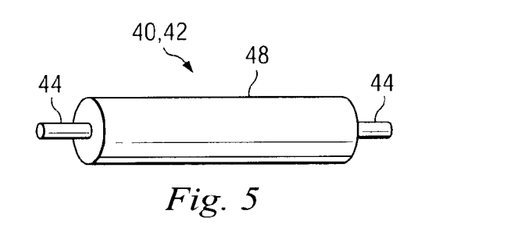

Referring to FIGS. 4 and 5, the bar-type rollers 40, 42 can have various shapes and can have different shapes from each other. For the sake of two examples, FIG. 4 shows the bar-type rollers 40, 42 with an axel 44 connected to an hourglass-shaped member 46, and FIG. 5 shows the bar-type rollers 40, 42 with the axel 44 connected to a cylindrical-shaped member 48. In some embodiment, the bar-type rollers can be formed of a single, homogenous material, while in other embodiments, the axel 44 can be separate from the member 46 or 48, whereby the member can move or roll around the axel.

Figure 6:
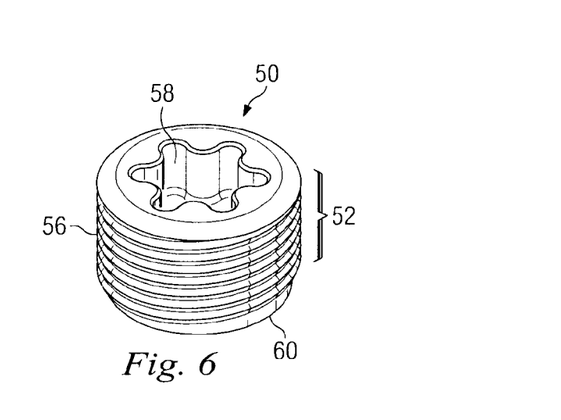
FIG. 6 is a perspective view of a coupling member capable of engaging with the attachment mechanism of FIG. 2.

Referring now to FIG. 6, in one embodiment, the coupling member 50 has a plug body 52 including a thread form 56. Plug body 52 further includes a tool receptacle 58 formed therein, and into which a driving tool can be received to apply a rotary driving force to engage coupling member 50 to thread forms 35a, 35b of anchor 30. Coupling member 50 also includes a lower bearing surface 60 which is configured to bear against the second bar-type roller 42 in the roller section 37. In some embodiments, the lower bearing surface 60 is configured to bear against the second bar-type roller 42 on the axel 44, while in other embodiments, the lower bearing surface bears against the member 46/48 of the bar-type roller.

Figure 7:
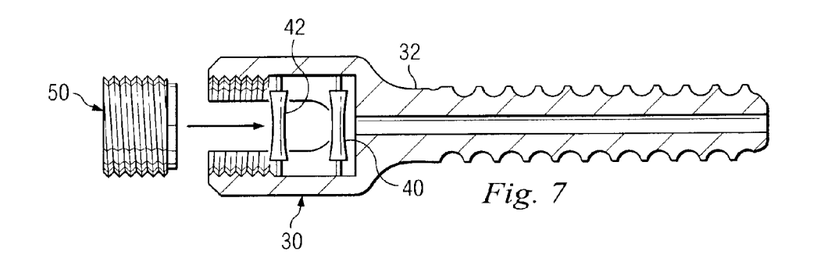
FIGS. 7, 8, and 10 are cross-sectional views of attachment mechanisms according to different embodiments of the invention.
Figure 8:
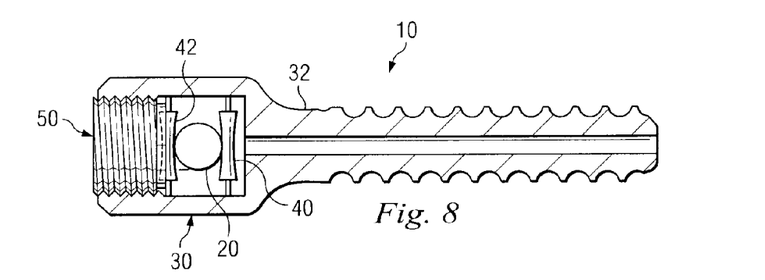

Referring to FIGS. 7 and 8, in operation, when the coupling member 50 is positioned inside the anchor 30, both bar-type rollers 40, 42 press against the rod 20 (FIG. 1) from opposing directions. The rod 20 is prevented from moving in any direction except one—it is allowed to move between the bar-type rollers 40, 42 in a direction perpendicular to the longitudinal axis of the shaft 32, while still maintaining a secure fixation between the rod 20 and the anchor 30. As a result, this allows the spinal fixation system 10 to secure the different vertebrae V1, V2, V3, V4, V5 for promoting fusion there between, but allow the overall length of the spinal segment to grow and/or otherwise change. In some embodiments, the bar-type rollers 40, 42 are relatively difficult to rotate, thereby providing a maximum amount of fixation. This can be achieved, for example, by a very tight frictional fit of the axes 44 of the two bar-type rollers 40, 42. In other embodiments, the bar-type rollers 40, 42 are more easy to rotate, thereby allowing the spinal fixation system 10 to allow some amount of flexion, extension, or other spinal movement.

Figure 9:
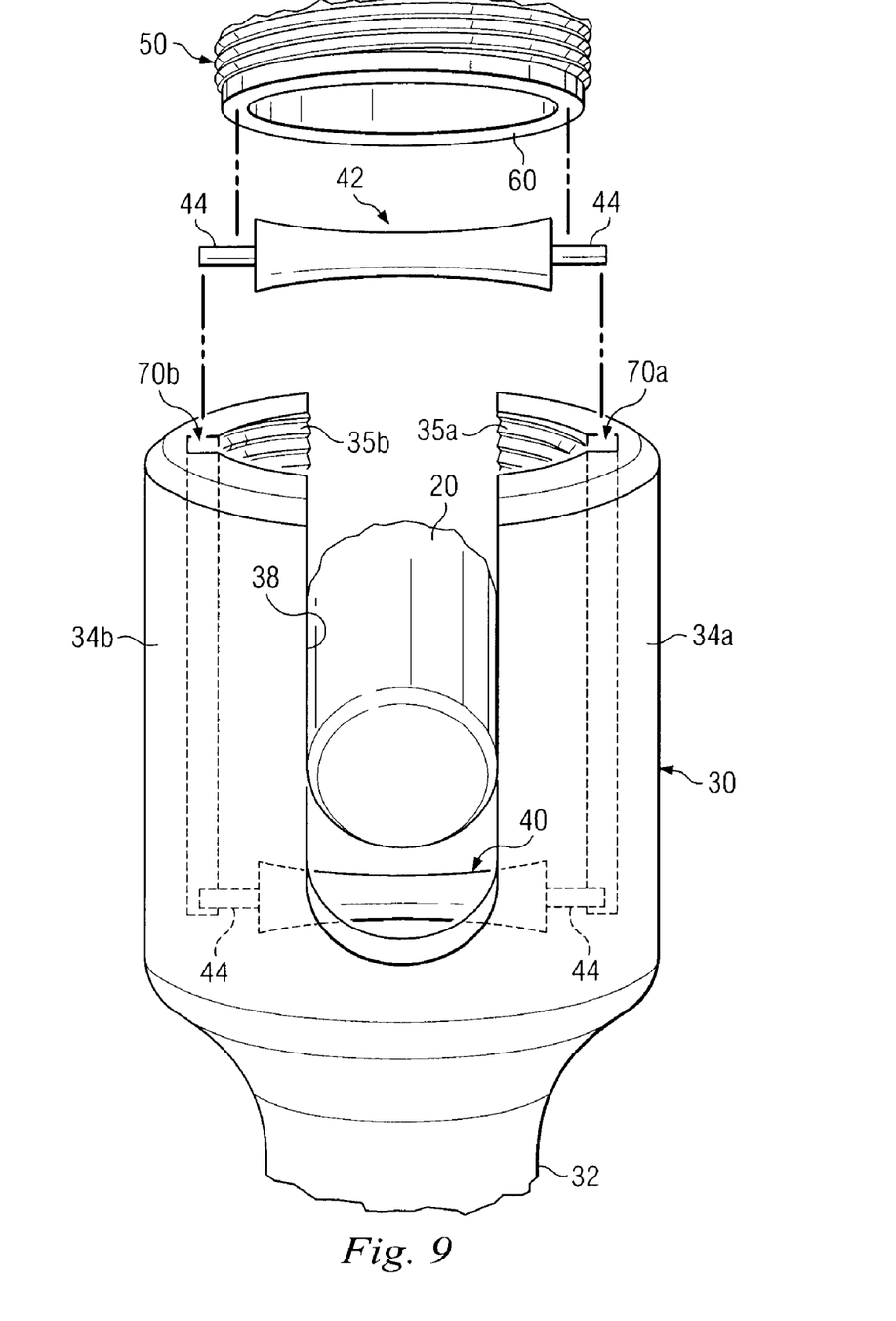
FIG. 9 is a perspective view of an attachment mechanism including a seat and a coupling member according to another embodiment of the invention.

Referring to FIG. 9, shown therein are various details of the anchor 30 and the coupling member 50 according to another embodiment of the present invention. This embodiment is similar to that of FIGS. 2-3, except that anchor 30 has two opposing grooves 70a, 70b in the arms 34a, 34b, respectively. The grooves allow one or both of the bar-type rollers 40, 42 to be positioned inside the U-shaped passage 38. In operation, the first bar-type roller 40 is positioned in the passage 38, followed by the rod 20, followed by the second roller 42. The assembly of bar-type rollers and rod can further be secured by the coupling member 50. In the present embodiment, the lower bearing surface 60 of the coupling member 50 presses against the axel 44 of the second bar-type roller 42.

In another embodiment, the first bar-type roller 40 can be permanently positioned in the passage 38, while the second bar-type roller 42 is added later. In this embodiment, the grooves 70a, 70b, can extend a shorter distance down into the passage 38, as shown in the Figure.

In another embodiment, both bar-type rollers 40, 42 can be permanently positioned in the passage 38. One or both of the bar-type rollers 40, 42 can still reside in shortened grooves 70a, 70b, but the shortened grooves would prevent the bar-type rollers from being removed from the anchor 30. This embodiment provides the benefit of having fewer separate parts, while still allowing the bar-type rollers to separate sufficiently for insertion of the rod 20, and then be pressed together sufficiently to secure the rod 20 in the passage 38 as described above.

In another embodiment, the second bar-type roller 42 can be part of a washer (not shown) associated with the coupling member 50. The washer could be attached to the coupling member 50, but still be rotatable inside the passage 38. The washer can also include the second bar-type roller 42 extended and positioned there across.

Figure 10:
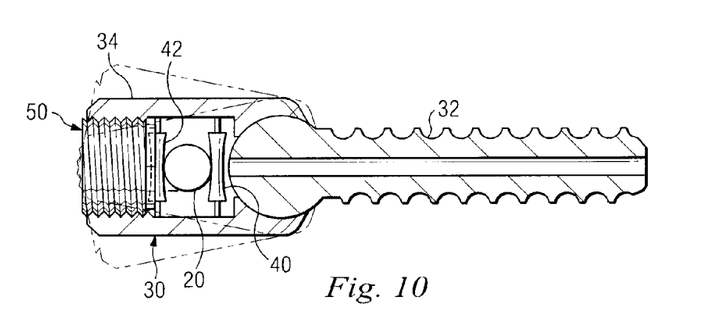

Referring to FIG. 10, in another embodiment, the seat 34 of the anchor 30 is selectively movable relative to the shaft 32. This can be provided, in some embodiments, by the shaft 32 having a rounded head that is allowed to rotate inside the seat 34. An example of such a multi-axial configuration between the seat 34 and the shaft 32 is provided in U.S. Pat. No. 5,624,442, which is hereby incorporated by reference.

Another embodiment of the anchor 30 and the coupling member 50, as used in the stabilization system 10 of FIG. 1, is described below with reference to FIGS. 11 and 12. For the sake of reference, this embodiment will be designated as anchor 130 and coupling member 150. Many components are the same from each group of embodiments, while other components are different, as discussed below.

Figures 11, 12:
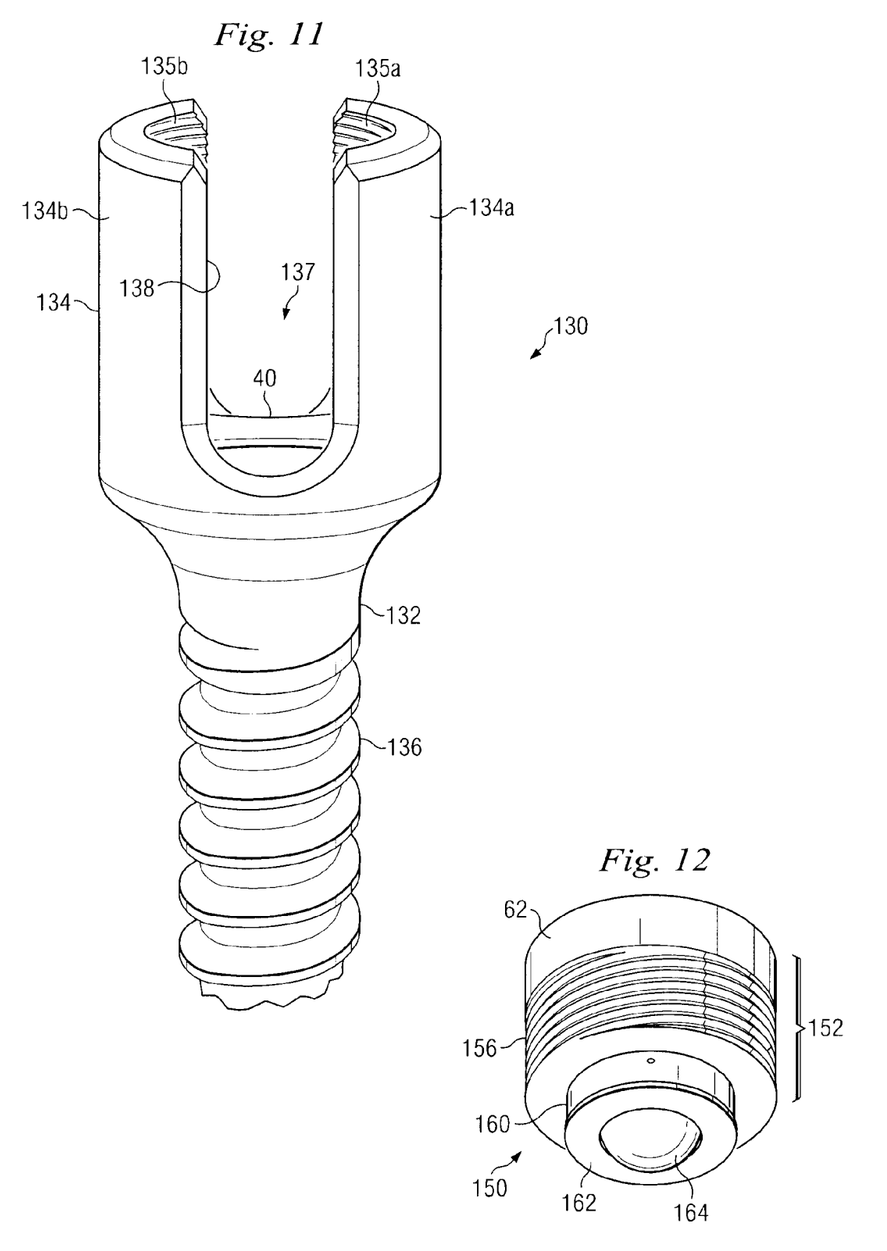
FIG. 11 is a perspective view of an attachment mechanism including a seat according to yet another embodiment of the invention.
FIG. 12 is a perspective view of a coupling member for use with the attachment mechanism of FIG. 10.

Referring now to FIG. 11, shown therein are various details of the anchor 130 according to another embodiment of the present invention. Anchor 130 includes an elongated shaft 132 and a rod receiving portion in the form of a seat 134. Shaft 132 can include an external thread form 136 in the form of a single thread turn or a plurality of discrete threads. Different or additional engaging structures along shaft 132 are also contemplated, such as barbs or pivoting gulls, so long as shaft 132 can engage the bony tissue of the vertebra to which anchor 130 is attached. In an alternate form, shaft 132 is in the form of a spinal hook.

In the illustrated embodiment, seat 134 includes a first arm 134a and a second arm 134b. The arms 134a, 134b define internally threaded sections 135a, 135b, respectively, and a roller section 137 positioned in a U-shaped passage 138 extending between the arms. The roller section 137 includes a first bar-type roller 40.

Referring now to FIG. 12, the coupling member 150 has a plug body 152 and a thread form 156 to engage coupling member to thread forms 135a, 135b of anchor 130. Coupling member 150 also includes a roller housing 160 and engaging lip 162 for rotatably securing a ball-type roller 164.

In operation, when the coupling member 150 is positioned inside the anchor 130, both the bar-type roller 40 and the ball-type roller 164 press against the rod 20 (FIG. 1) from opposing directions. The rod 20 is allowed to move between the ball-type roller 164 and the bar-type roller 40 in a direction perpendicular to the longitudinal axis of the shaft 132, while still maintaining a secure fixation between the rod 20 and the anchor 130. As a result, this allows the spinal fixation system 10 to secure the different vertebrae V1, V2, V3, V4, V5 for promoting fusion there between, but also allows the overall length of the spinal segment to grow and/or otherwise change. In some embodiments, one or both of the rollers 40, 164 are relatively difficult to rotate, thereby providing a maximum amount of fixation. This can be achieved, for example, by a very tight frictional fit. In other embodiments, the rollers 40, 164 are more easy to rotate, thereby allowing the spinal fixation system 10 to allow some amount of flexion, extension, or other spinal movement.

Figure 13:
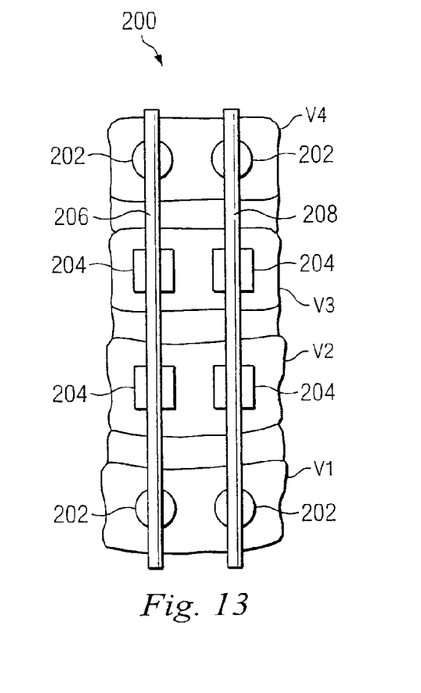
FIGS. 13-15 are block diagrams of spinal fixation systems according to various embodiments of the present invention.

Referring now to FIG. 13, in another embodiment, a spinal stabilization system 200 is shown having a combination of one or more slidable anchors 202, such as one or more of the anchors described above, and one or more fixed anchors 204, such as those disclosed in U.S. Publication No. 2004/0172025, which is hereby incorporated by reference. The anchors 202, 204 are secured to and interconnected by rods 206 and 208. In this embodiment, the slidable anchors 202 are connected to vertebrae V4 and V1, and the fixed anchors 204 are connected to vertebrae V3 and V2. In this system 200, the grown or movement is allowed by the slidable anchors 202 for the vertebrae V4 and V1, while the remaining vertebrae remain in a fixed relationship.

Figure 14:
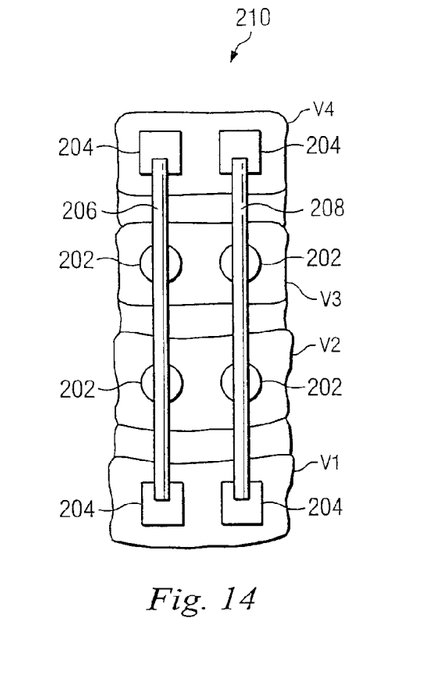

Referring to FIG. 14, in another embodiment, a spinal stabilization system 210 is shown having a combination of one or more slidable anchors 202, and one or more fixed anchors 204. The anchors 202, 204 are secured to and interconnected by rods 206 and 208. In this embodiment, the slidable anchors 202 are connected to vertebrae V3 and V2, and the fixed anchors 204 are connected to vertebrae V4 and V1. In this system 210, the grown or movement is allowed by the slidable anchors 202 for the vertebrae V2 and V3, while the remaining vertebrae remain in a fixed relationship.

Figure 15:
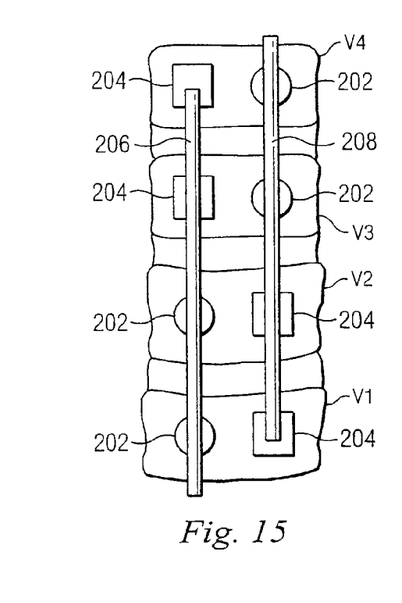
Figure 16:
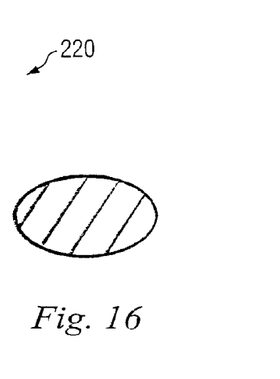
FIG. 16 is a cross-sectional view of an example of a non-circular rod.

Referring to FIG. 15, in another embodiment, a spinal stabilization system 220 is shown having a combination of one or more slidable anchors 202, and one or more fixed anchors 204. Each vertebrae V1, V2, V3, V4 includes a slidable anchor and a fixed anchor. In this system 220, the grown or movement is allowed by the slidable anchors 202 for the vertebrae V2 and V3, while the remaining vertebrae remain in a fixed relationship.

Additional changes may also be provided to one or more of the above-described embodiments. For one, the rod 20 in FIG. 1 can have various shapes. In FIG. 2, the rod 20 is shown to have a circular cross section. In other embodiments, the rod 20 can have a square, rectangular, oval, or some other non-uniform cross section. In these embodiments, the rod would still be allowed to have linear motion as described above, but the shape of the rod 20 would prevent rotation relative to the anchors 30. In another embodiment, the rod 20 can have a non-uniform shape that changes (e.g., spirals) along the length of the rod. Continuing with the spiral example, the spiraled shape induces torsion with linear motion. Therefore, as the patient grows, the curvature of the spiraled rod 20 causes the rod to rotate. This may be desirable, for further example, in dealing with diseased spinal formations such as scoliosis. Furthermore, the anchor 30 may, in some embodiments, not include any rollers, but may have a shape, such as a "C" shape, tie-rod shape, or sag rod shape, that is adapted to both secure the rod 20 in some directions while still allowing linear motion of the rod.

Although only a few exemplary embodiments have been described in detail above, those skilled in the art will readily appreciate that many modifications are possible in the exemplary embodiments without materially departing from the novel teachings and advantages of this disclosure. Accordingly, all such modifications and alternative are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure. It is understood that all spatial references, such as "horizontal," "vertical," "top," "upper," "lower," "bottom," "left," "right," "anterior," "posterior," "superior," "inferior," "upper," and "lower" are for illustrative purposes only and can be varied within the scope of the disclosure. In the claims, means-plus-function clauses are intended to cover the elements described herein as performing the recited function and not only structural equivalents, but also equivalent elements.

What is claimed is:

1. A system for stabilizing a spinal motion segment, comprising:
a rod sized to span a distance between a plurality of vertebrae of the spinal motion segment; and
a plurality of attachment mechanisms for securing the rod to the plurality of vertebrae;
wherein each of the plurality of attachment mechanisms includes a seat for securing to the rod and a vertebrae engaging member for securing to the vertebrae, the seat of the attachment mechanism comprising a seat passage sized and arranged to receive the rod in a manner that the red extends through the passage; and
wherein at least one of the attachment mechanisms includes a first movement mechanism for allowing the rod to move in a linear direction in the seat passage, the first movement mechanism comprising a roller arranged within the seat to form at least a part of the seat passage, the roller having a roller outer surface arranged to contact and roll along the rod as the rod moves in the linear direction in the seat passage, the roller being positioned at a bottom of the seat such that the roller outer surface forms one side of the seat passage and sides of the seat form two opposing surfaces of the seat passage.

2. The system of claim 1 wherein the first movement mechanism includes a bar-type roller attached to the at least one attachment mechanism.

3. The system of claim 1 wherein the at least one of the attachment mechanisms includes a coupling member for selectively securing the rod to the seat.

4. The system of claim 3 wherein the coupling member is integral with the first movement mechanism.

5. The system of claim 1 wherein the at least one of the attachment mechanisms includes a second movement mechanism for allowing the rod to move in the linear direction relative to the attachment mechanism.

6. The system of claim 5 wherein at least one of the two movement mechanisms is a bar-type roller.

7. The system of claim 5 wherein at least one of the two movement mechanisms is a ball-type roller.

8. The system of claim 1 wherein at least one of the attachment mechanisms is configured to prevent relative movement between it and the rod in any direction.

9. The system of claim 1 wherein the vertebrae engaging member is a pedicle screw or a spinal hook.

10. The system of claim 1 wherein the seat of the at least one attachment mechanism includes at least one groove for receiving the roller.

11. The system of claim 10 wherein the roller is a bar-type roller and the seat of the at least one attachment mechanism includes opposing grooves for receiving an axel of the bar-type roller.

12. The system of claim 5 wherein the first and second movement mechanisms are respective first and second bar-type rollers and the seat of the at least one attachment mechanism includes opposing grooves for receiving an axel of at least one of the first and second bar-type rollers.

13. The system of claim 12 wherein the grooves extend to an exterior surface of the seat by which at least one of the two bar-type rollers can be selectively placed in the groove for engagement with the rod.

14. A system for stabilizing a spinal motion segment, comprising:
a rod sized to span a distance between a first and second vertebrae of the spinal motion segment;
a first anchor for securing the rod to the first vertebrae; and
a second anchor for securing the rod to the second vertebrae;
wherein the first anchor includes a first vertebrae engaging member for securing to the first vertebrae and a first seat for communicating with the rod, the seat comprising a seat passage sized and arranged to receive the rod in a manner that the rod extends through the passage, the first seat including a first movement mechanism for allowing the rod to move in a transverse direction relative to the first vertebrae engaging member, the first movement mechanism comprising a roller arranged within the seat to form at least a part of the seat passage, the roller having a roller outer surface arranged to contact and roll along the rod as the rod moves in the transverse direction in the seat passage, the roller being positioned at a bottom of the seat such that the roller outer surface forms one side of the seat passage and sides of the seat form two opposing surfaces of the seat passage.

15. The system of claim 14 wherein the rod has a circular cross-section.

16. The system of claim 14 wherein the second anchor includes a second vertebrae engaging member for securing to the second vertebrae and a second seat for communicating with the rod.

17. The system of claim 16 wherein the second seat includes a second movement mechanism for allowing the rod to move in a transverse direction relative to the second vertebrae engaging member.

18. The system of claim 14 wherein the passage is defined by first and second arms of the first seat.

19. The system of claim 18 wherein the first and second arms of the first seat include threads for receiving a coupling member, the coupling member being selectively engagable with the first seat to allow the rod to be configured in the passage and to allow the rod to be secured in the passage.

20. The system of claim 19 wherein the coupling member includes a second movement mechanism, the second movement mechanism comprising a roller for allowing the rod to move in a transverse direction relative to the first vertebrae engaging member.

21. The system of claim 18 wherein the first movement mechanism is a first roller, and wherein the first and second arms are configured to support the first roller for extending across the passage.

22. The system of claim 21 wherein the first and second arms are configured to support a second roller for extending across the passage.

23. The system of claim 22 wherein the first and second rollers are bar-type rollers and the first and second arms are configured to engage with an axel of the bar-type rollers.

24. The system of claim 21 wherein the second movement mechanism is a second roller is a bar-type roller and the coupling member is adapted to engage with an axel of the bar-type roller.

25. The system of claim 14 wherein the rod is sized to also span a third vertebrae, the system further comprising:
a third anchor for securing the rod to the third vertebrae;
wherein the second anchor includes a second vertebrae engaging member for securing to the second vertebrae and a second seat for communicating with the rod, the second seat including a second movement mechanism for allowing the rod to move in a transverse direction relative to the second vertebrae engaging member.

26. The system of claim 25 wherein the third anchor is configured to prevent relative movement between it and the rod.

27. The system of claim 25 wherein the second vertebrae is between the first and third vertebra.

28. The system of claim 14 wherein the rod is sized to also span a third vertebrae, the system further comprising:
a third anchor for securing the rod to the third vertebrae;
wherein the second anchor is configured to prevent relative movement between it and the rod, and
wherein the third anchor is configured to prevent relative movement between it and the rod.

29. The system of claim 27 wherein the first vertebrae is between the second and third vertebra.

30. The system of claim 14 wherein the rod has a non-circular cross-section.

31. A system for stabilizing a spinal motion segment, comprising:
a rod sized to span a distance between a plurality of vertebrae of the spinal motion segment; and
a plurality of bone anchors for securing the rod to the plurality of vertebrae;
wherein each of the plurality of bone anchors includes a seat for securing to the rod and a vertebrae engaging member for securing to the vertebrae, the seat including a first arm and a substantially parallel second arm defining a substantially U-shaped seat passage therebetween, the seat also including a groove extending along an inner surface of at least one of the arms, the seat passage being shaped to receive the rod; and
wherein at least one of the attachment mechanisms includes a bar-type roller disposed within the seat at the bottom of the U-shaped passage to form at least a portion of the seat passage, the bar-type roller being disposed such that a portion of the roller extends into and is maintained in place by the groove in the arm, the bar-type roller extending substantially transverse to the direction of the rod such that the rod contacts the roller when the rod is disposed within the seat passage, the roller having a roller outer surface configured to directly contact the outer surface of the rod and to roll along the rod as the rod moves in the linear direction through the seat passage.

32. The system of claim 31, wherein the plurality of bone anchors include at least one of a spinal hook and a pedicle screw.

33. The system of claim 31, further comprising a coupling member that couples the rod into the seat, the coupling member engaging both the first and second arms in a manner that prevents removal of the rod from the seat, the coupling member also being associated with a second roller having a second roller outer surface configured to directly contact the outer surface of the rod and to roll along the rod as the rod moves in the linear direction through the seat passage.

34. The system of claim 1, wherein the at least one attachment mechanism comprises first and second arms extending substantially parallel to each other, the first and second arms each including a concave inner surface having threading formed thereon, at least one of the first and second arms having a groove extending into the threading on the inner surface, the roller being disposed such that a portion of the roller extends into and is maintained in place by the groove in the at least one of the first and second arms.

35. The system of claim 14, wherein the first anchor comprises first and second arms extending substantially parallel to each other, the first and second arms each including a concave inner surface having threading formed thereon, at least one of the first and second arms having a groove extending into the threading on the inner surface, the roller being disposed such that a portion of the roller extends into and is maintained in place by the groove in the at least one of the first and second arms.

* * * * *